(12) United States Patent
Loh et al.

(10) Patent No.: US 6,582,748 B1
(45) Date of Patent: Jun. 24, 2003

(54) FAT COMPOSITIONS CONTAINING WAXES

(75) Inventors: Willie H-T Loh, Minneapolis, MN (US); Linsen Liu, Irvine, CA (US); Daniel S. Lampert, Chaska, MN (US)

(73) Assignee: Cargill Incorporated, Wayzata, MN (US)

( * ) Notice: Subject to any disclaimer, the term of this patent is extended or adjusted under 35 U.S.C. 154(b) by 0 days.

(21) Appl. No.: 09/569,887

(22) Filed: May 12, 2000

Related U.S. Application Data
(60) Provisional application No. 60/134,751, filed on May 18, 1999.

(51) Int. Cl.⁷ .............................................. A23D 9/007
(52) U.S. Cl. ....................................... 426/601; 426/611
(58) Field of Search .................................. 426/601, 611

(56) References Cited

U.S. PATENT DOCUMENTS

| | | | |
|---|---|---|---|
| 4,272,447 A | | 6/1981 | Beharry |
| 4,753,807 A | | 6/1988 | Fuseya et al. |
| 4,793,991 A | | 12/1988 | Slimak et al. |
| 4,839,184 A | | 6/1989 | Cherukuri et al. |
| 4,839,192 A | * | 6/1989 | Sagi et al. .................. 426/607 |
| 4,917,915 A | | 4/1990 | Cain et al. |
| 5,338,564 A | | 8/1994 | Meyer et al. |
| 5,431,840 A | | 7/1995 | Soldanski et al. |
| 5,482,633 A | | 1/1996 | Muraldihara et al. |
| 5,660,865 A | | 8/1997 | Pedersen et al. |
| 5,882,657 A | | 3/1999 | Miguel-Colombel et al. |
| 6,013,818 A | * | 1/2000 | O'Lenick, Jr. .............. 554/224 |
| 6,022,578 A | * | 2/2000 | Miller ......................... 426/603 |
| 6,180,668 B1 | * | 1/2001 | O'Lenick et al. ........... 514/547 |
| 6,258,965 B1 | * | 7/2001 | O'Lenick, Jr. .............. 554/227 |
| 6,306,906 B1 | * | 10/2001 | Wohlman et al. ........... 514/552 |
| 6,322,843 B1 | | 11/2001 | Schuurman et al. |

FOREIGN PATENT DOCUMENTS

| | | |
|---|---|---|
| EP | 1 080 643 A1 | 3/2001 |
| GB | 1 277 981 | 6/1972 |
| WO | WO 95/28847 | 11/1995 |

OTHER PUBLICATIONS

Hui (ed.), *Bailey's Industrial Oil and Fat Products*, Fifth Edition, vol. 1, 1996, John Wiley & Sons, Inc., New York, pp. 444–447.

Baldwin (ed.), Seventh International Conference on Jojoba and Its Uses, 1988 Proceedings, AOCS, Champaign, IL, pp. 354–363.

"Dietary fat intake and the risk of coronary heart disease," *New England J. Med.*, Nov. 1977.

Doss, "Properties of the Principal Fats, Fatty Oils, Waxes, Fatty Acids and Their Salts," Technical and Research Division of The Texas Company, 1952.

Hui (ed.), *Bailey's Industrial Oil & Fat Products*, 1996, John Wiley & Sons, Inc., Fifth Edition, vol. 2, pp. 401–402 and 642–645.

Hui (ed.), *Bailey's Industrial Oil & Fat Products*, 1996, John Wiley & Sons, Inc., Fifth Edition, vol. 4, pp. 403.

Lichtenstein, "Trans Fatty Acids, Plasma Lipid Levels, and Risk of Developing Cardiovascular Disease," American Heart Association Medical/Scientific Statement; 1997.

"Position paper on trans fatty acids 1–3," Special Task Force Report, *Am. J. Clin. Nutr.*, 1996, vol. 63, 11 pgs.

\* cited by examiner

*Primary Examiner*—Carolyn Paden
(74) *Attorney, Agent, or Firm*—Fish & Richardson P.C., P.A.

(57) ABSTRACT

Fat compositions that contain a vegetable oil and a plant-derived wax component are described. Food and cosmetic products containing such fat compositions also are described.

27 Claims, 1 Drawing Sheet

FAT COMPOSITIONS CONTAINING WAXES

CROSS-REFERENCE TO RELATED APPLICATIONS

This application claims priority from U.S. Provisional Application No. 60/134,751, filed May 18, 1999.

TECHNICAL FIELD

The invention relates to compositions that include a vegetable oil and a plant derived wax component.

BACKGROUND

Hydrogenation of an oil increases the saturated fatty acid content of the oil, while decreasing the unsaturated fatty acid content. During the hydrogenation process, trans fatty acids also are formed. The extent of saturation and trans formation depends on the hydrogenation reaction conditions, including type of catalyst, reaction temperature, and reaction time. Hydrogenation is used to increase shelf-life of oil products and to increase functionality. In general, harder products such as stick margarine have a higher trans fatty acids content than softer products such as soft tub margarine. As saturated and trans fatty acids intake have been linked to increased serum cholesterol levels in humans, it is generally recommended that intake of saturated and trans fatty acids be limited.

SUMMARY

The invention is based on the discovery that blends of vegetable oil and plant-derived waxes can be used to formulate low calorie, low saturated, and low trans fatty acid food products. Addition of low levels of plant-derived wax solidifies liquid oils, simulating the hardening effects of hydrogenation. Thus,.food products prepared from compositions of the present invention provide a useful alternative to food products that contain a high content of saturated and/or trans fatty acids, such as shortening and margarine.

In one aspect, the invention features compositions that include a vegetable oil and a plant-derived wax component and that have a melting point of about 5° C. to about 50° C. or at least about 46° C. For example, the composition can have a melting point of at least about 52° C. or about 60° C., or about 46° C. to about 75° C. The plant-derived wax component can be selected from the group consisting of sunflower oil wax, rice bran wax, hydrogenated jojoba oil, and corn oil wax. Sunflower oil wax is particularly useful. The plant-derived wax component can be about 0.1% to about 30%, by weight, of a composition. For example, the plant-derived wax component can be about 0.5% to about 15%, about 0.5% to about 7.5%, about 1% to about 5%, or about 2% to about 4%, by weight, of the composition.

The vegetable oil can be selected from the group consisting of rapeseed oil, soybean oil, sunflower oil, palm oil, safflower oil, coconut oil, palm kernel oil, sesame oil, peanut oil, cottonseed oil, and corn oil. Rapeseed oil, and in particular, canola oil, is suitable for use in compositions of the invention. Compositions of the invention can have a low saturated or trans fatty acids content. For example, the composition can have a trans fatty acids content of less than about 3%, a trans fatty acids content of about 0%, or a saturated fatty acid content of less than 7%. The invention also features a margarine or shortening that includes such compositions.

The invention also features a composition that includes an interesterified vegetable oil and plant-derived wax component. The plant-derived wax component is at least about 0.1%, by weight, of such a composition, e.g., 0.5% to 30% or 0.5% to 15%. Suitable vegetable oils and plant-derived waxes are described above, and can be either chemically or enzymatically interesterified. An interesterified composition can have a solid fat content of less than about 8% or 6% at 10° C. For example, the solid fat content can be about 1% to about 6% at 10° C.

In another aspect, the invention features a composition that includes a vegetable oil from a first plant species and a plant-derived wax component from a second plant species. The plant-derived wax component is at least about 0.1%, by weight, of the composition. The plant-derived wax component can be sunflower oil wax and the vegetable oil can be selected from the group consisting of rapeseed oil, soybean oil, palm oil, safflower oil, coconut oil, palm kernel oil, sesame oil, peanut oil, and corn oil.

The invention also features a method for making a composition that includes blending a vegetable oil and a plant-derived wax component, wherein the plant-derived wax component is at least about 0.5%, by weight, of the composition. As described above, the wax component can be about 0.5% to about 15%, by weight, of the composition.

The invention features a composition made by combining a vegetable oil and a plant-derived wax component. The plant-derived wax component is at least about 0.5%, by weight, of the composition, as described herein.

The invention also features a food product that includes a fat composition. The fat composition includes a vegetable oil and a plant-derived wax component, wherein the plant-derived wax component is at least about 0.1%, by weight, of the fat composition. The food product can be a microwave popcorn product, wherein the microwave popcorn product includes a plurality of unpopped popcorn kernels suspended in a fat composition. The fat composition includes a vegetable oil and a plant-derived wax component, which is at least about 0.1%, by weight, of the composition. The plant-derived wax component can be, for example, about 1% to about 2%, by weight, of the composition.

In yet another aspect, the invention features a cosmetic product that includes a fat composition, wherein the fat composition includes a vegetable oil and a plant-derived wax component, the wax component comprising at least about 0.1%, by weight, of the composition (e.g., about 0.5% to about 30%).

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
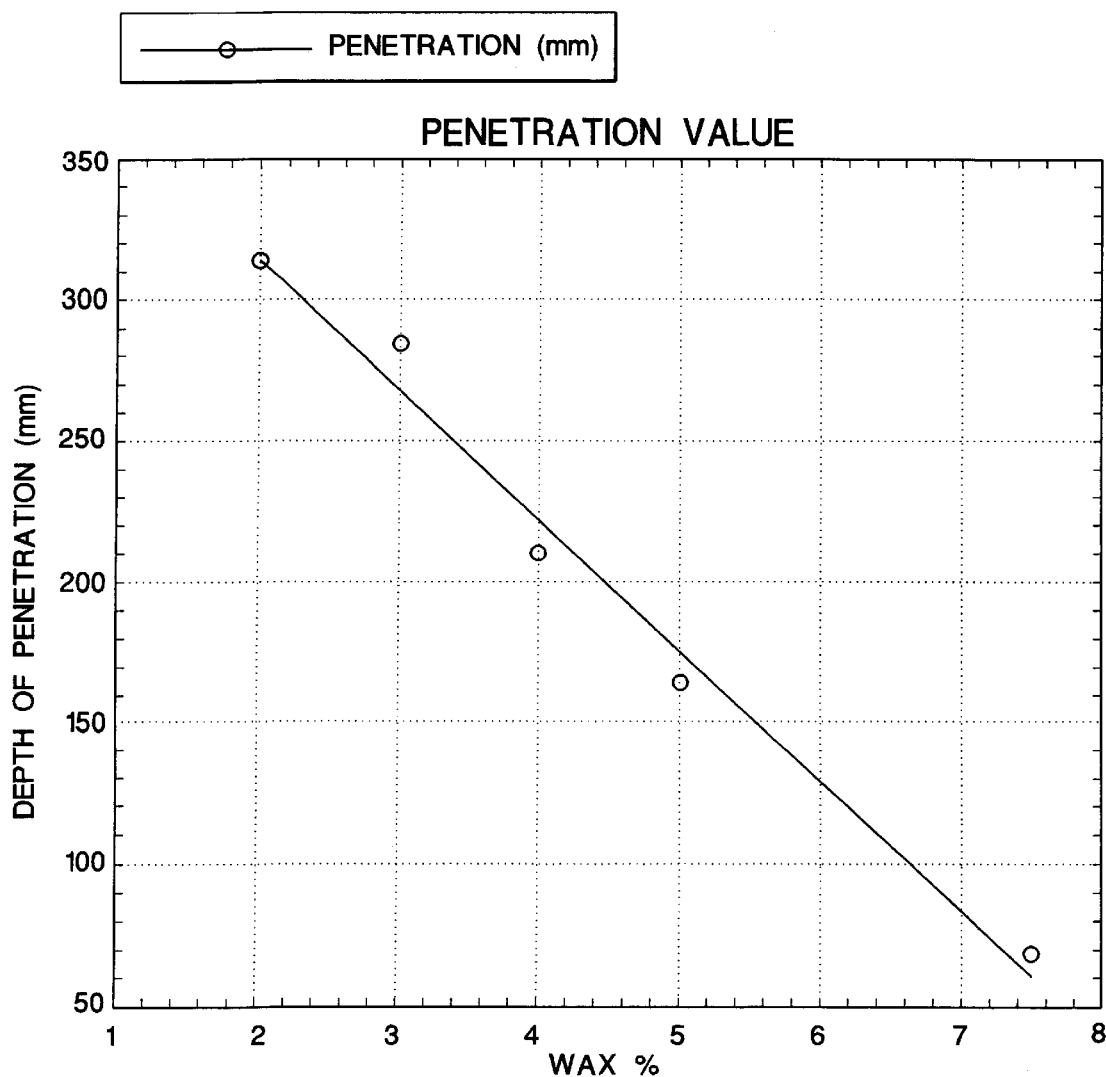
FIG. 1 is a graph that indicates the penetration depth of a cone into sunflower oil wax and canola oil blends.

The invention features fat compositions that include vegetable oil and a plant-derived wax component. As used herein, "plant-derived wax component" refers to any component containing waxes isolated from plants. A plant-derived wax component includes at least 0.25% wax, and may contain up to 99% wax. In general, wax is a collective term for a group of compounds that contain long-chain fatty acids esterified with a fatty alcohol, with total carbon chains generally ranging from about 20 to about 44 carbons in length. Waxes have melting points of at least 40° C. Plants synthesize waxes for use as barriers to moisture evaporation and penetration, with the exception of jojoba (*Simmondsia chinensis*), which stores waxes as an energy source. Suitable plant-derived waxes include, for example, sunflower oil wax (*Helianthus annuus*), rice bran oil wax, and corn oil wax. Hydrogenated jojoba oil also is a suitable plant-derived wax.

Crude sunflower oil typically contains up to about 1% of wax, depending on the variety and on growing and processing conditions. The wax content of crude sunflower oil is dependent on the dehulling process, as sunflower wax is thought to originate from wax deposited on seed hulls. Purified sunflower oil wax has a melting point of about 70° C. to about 80° C., and is primarily composed of long chain saturated fatty acid hydrocarbons and long chain alcohols. In some embodiments, sunflower oil that has not been dewaxed, i.e., retains endogenous wax content, also may be used directly in formulating a food or non-food product.

Jojoba produces and stores liquid wax as the major component of its seed storage lipid. Typically, waxes isolated from jojoba oil are esters of very long-chain monoenoic fatty acyl groups (C20 to C26) and monounsaturated alcohols (C20 to C22). A major component of jojoba wax is cis-13-docosenyl cis-11-eisosenoate. Non-hydrogenated jojoba oil is liquid and has an iodine value ranging from about 80 to about 85. Jojoba oil can be hydrogenated by methods known in the art to obtain a wax suitable for use in the invention.

Rice bran oil (also called rice oil) is a by-product of rice milling, and contains approximately 2% to 5% wax, depending on process conditions. For example, extraction of the oil at 50° C. yields up to three times more wax than extraction at 20° C. Rice bran oil wax typically has a melting point of about 75° C. to about 80° C. and an iodine value of about 11 to about 18. See, *Bailey's Industrial Oil & Fat Products*, Hui, Y. H., 1996, John Wiley & Sons Inc., New York, N.Y., Vol. 2, pp. 401–402. Rice bran oil that has not been dewaxed also can be used directly for certain applications.

Plant-Derived Waxes

As many plants coat their seed with a thin layer of wax, waxes are unavoidably extracted with the oils. Due to their high melting points and limited solubility in oil, waxes cause a cloudy appearance in vegetable oils and are often removed from oils. Thus, plant-derived waxes can be obtained as a by-product of oil processing. In general, waxes are removed from vegetable oils by cooling the oil and filtering immediately, or by cooling the oil, allowing the wax to crystallize, then filtering. Filter aids such as diatomaceous earth, which also are used to precoat filter screens, can be added in proportionate amounts to facilitate removal of wax. For example, oil can be cooled to about 0° C. and a filter aid can be added, e.g., approximately 0.63% of filter aid, based on the weight of the oil, can be added to sunflower oil containing about 0.5% wax. After mixing the oil and filter aid, the mixture is pumped through a filter to provide dewaxed oil and a waxy cake. The filter aid can be removed from the waxy cake by mixing with a hot oil, and filtering through a small pressure leaf filter to provide a plant derived wax component containing an oil-wax mixture. An oil-wax mixture obtained in this manner is suitable for use in the invention.

A centrifugal process also can be used to dewax vegetable oils containing high wax contents. This process generally entails chilling alkali neutralized oil to allow wax particles to crystallize. Chilled water is added to the mixture, and the mixture is heated. Centrifugation of the heated mixture removes waxes, providing a plant-derived wax component that is suitable for use in the invention.

Alternatively, wax can be obtained from vegetable oils according to the method of U.S. Pat. No. 5,482,633, which allows crystallized waxes to be separated from the oil without the use of substances such as diatomaceous earth. In this method, vegetable oils are heated to a temperature above the melting point of the higher melting glycerides in the oil, then rapidly cooled and allowed to mature at a temperature of about 16° C. or less for at least about 6 hours to permit the wax in the oil to crystallize, and filtering the vegetable oil/particulate wax blend through a porous nonmetallic inorganic filter to obtain a plant-derived wax component. When sunflower oil is dewaxed according to this method, sunflower oil is obtained with typically less than 10 ppm wax. The by-product of this processing, sunflower oil containing approximately 1% wax, can be used directly to formulate products or can be further enriched for wax content by repeating the crystallizing and filtering steps described above.

Preparation of Compositions

Compositions of the invention can be obtained by blending a vegetable oil and a plant-derived wax component. In general, the plant-derived wax component is heated above its melting point, the vegetable oil is added, and the mixture is stirred for about 5 to about 30 minutes or until a uniform composition is obtained. Typically, the vegetable oil has been refined, bleached, and deodorized prior to blending with the wax component. Nonlimiting examples of vegetable oil include rapeseed oil (Brassica), soybean oil (Glycine), sunflower oil (*Helianthus annuus*), palm oil (*Elaeis guineensis* Jacq.), safflower oil (Carthamus), coconut oil (*Cocos nucifera*, L.), palm kernel oil, sesame oil (Sesamum), peanut oil (*Arachis hypogaea* L.), cottonseed oil (Gossypium), olive oil (Olea), linseed oil, grapeseed oil, crambe oil, and corn oil (*Zea mays*). Rapeseed oil includes high erucic acid rapeseed (HEAR) oil and canola oil, which has less than 2% erucic acid. Suitable canola oils can have an oleic acid content ranging from about 60% to about 90%. Use of mid to high oleic acid canola oils (i.e. 74–90% oleic acid) typically will impart suitably high oxidative stability to fat compositions of the invention.

The compositions can contain a plant-derived wax component from a first plant species and a vegetable oil from the same or a second plant species. The plant-derived wax and vegetable oil can be from different genera, e.g., a composition can contain sunflower oil derived wax and a vegetable oil extracted from rapeseed, including *Brassica napus, Brassica campestris* (*Brassica rapa*), and *Brassica juncea,* soybean such as *Glycine max,* palm and palm kernel, safflower including *Carthamus tinctorius* and *C. oxyacantha,* coconut, sesame including *Sesamum indicum* L., *S. capense, S. schenkii, S. laciniatum, S. anglolense, S. prostratus, S. occidentale,* and *S. radiatum,* peanut, cottonseed including *Gossypium hirsutum* and *G. barbadense,* or corn. When the composition contains a plant-derived wax component and a vegetable oil from the same species, the plant-derived wax component is present at a level that is increased from the native vegetable oil.

A fat composition of the invention can be interesterified (i.e., an acyl group of one ester is exchanged with that of another ester) chemically or enzymatically. Thus, acyl groups of the triacylglycerols (TAGs) in the vegetable oil are exchanged with acyl groups from the waxes. Chemical interesterification generally is performed by first drying the blended fat compositions at about 105° C. to about 110° C. under vacuum for about 30 minutes to about 1 hour, then cooling to about 100° C. to about 105° C. Reactions are initiated by addition of catalyst, with development of an orange-brown color indicative of initiation of interesterification. Non-limiting examples of catalysts include base catalysts such as sodium methoxide, sodium ethoxide, sodium hydroxide, and glycerol. Metals such as sodium and magnesium, and metal hydrides also are useful catalysts.

Reactions typically are continued for 30 minutes to ensure completion. Progress of the reaction can be monitored using standard techniques such as differential scanning calorimetry, high performance liquid chromatography, infrared spectrometry, thin layer chromatography, Raman spectroscopy, or UV absorption. Upon completion of the reaction, catalysts such as sodium methoxide can be inactivated, for example, by addition of water, aqueous ammonium chloride, or citric acid, such as a 10% citric acid solution. Deactivated catalyst and soaps can be removed by a water wash, followed by centrifugation. The interesterified composition can be dried by addition of anhydrous magnesium sulfate or sodium sulfate, or dried at about 100° C. to about 105° C. under vacuum (e.g., <20 mmHg) for about 30 minutes.

Characterization of Fat Compositions

Blended compositions of the invention can have melting points that are at least about 5° C., e.g., at least about 10° C., 15° C., 20° C., 25° C., 30° C., 35° C., 40° C., 46° C., 50° C., 52° C., or 60° C. In particular, the composition can have a melting point that ranges from about 5° C. to about 50° C. or about 46° C. to about 75° C., depending on wax content. For example, a fat composition containing about 7.5% of sunflower oil wax or rice bran wax and vegetable oil has a melting point of about 72° C. A composition containing about 1% sunflower oil wax and vegetable oil (e.g., canola oil) has a melting point of about 60° C., whereas refined, bleached, and deodorized canola oil has a melting point of about −6° C. Compositions with melting points of about 50° C. or less typically are useful for food applications, while compositions with melting points greater than about 50° C. are used for non-food applications. Melting points of interesterified compositions are lower than blended compositions. For example, an interesterified composition can have a melting point that ranges from about 35° C. to about 60° C., depending on wax content. In particular, an interesterified composition containing about 10% sunflower oil wax and a vegetable oil has a melting point of about 52° C., wherein an interesterified composition containing about 1% sunflower oil wax and vegetable oil can have a melting point of about 35° C. to about 45° C. Melting points referred to herein are determined by differential scanning calorimetry (DSC) using a Perkin Elmer Model 7 differential scanning calorimeter. It is apparent, however, that melting points can be determined by other techniques, including Mettler Drop Point and visual inspection of material in a capillary tube in a water or oil bath.

Compositions of the invention typically contain at least 0.1%, by weight, of a plant-derived wax component. For example, the composition can have about 0.1% to about 0.5%, about 0.1% to about 1.0%, about 0.1% to about 7.5%, about 0.1% to about 10%, about 0.1% to about 20%, 0.3% to about 1%, about 0.3% to about 10%, about 0.3% to about 20%, about 0.5% to about 30%, about 0.5% to about 15%, about 0.5% to about 10%, about 1% to about 7.5%, about 1% to about 5%, or about 2% to about 4% of a plant-derived wax component, by weight, depending on the desired application. Fat compositions of the invention having wax contents greater than about 15%, e.g., about 20% to about 30%, typically are interesterified to reduce the melting point of the composition.

Compositions of the invention can have a solid fat content of about 0.1% to about 20% (e.g. 0.1% to 12%) at 10° C., and can be blended to obtain a desired solid fat content for products such as shortening and margarine. For example, all-purpose shortening can have a solid fat content as high as about 35%, with an average solid fat content of about 25%–30% at 10° C. Solid fat is an indicator of the percent of solid fat present over a defined temperature scale and can be measured by Solid Fat Index (SFI) or by Solid Fat Content (SFC). SFC typically is measured by pulsed nuclear magnetic resonance (NMR). See, AOCS Official Method Cd 16b-93. SFI generally is measured by dilatometry and utilizes a series of temperature-controlled baths at 10, 21.1, 26.7, 33.3, and 40° C. and glass dilatometers for determining volume of the sample at each temperature. See, *Bailey's Industrial Oil & Food Products,* Fifth Edition, John Wiley & Sons, Inc., Vol. 4, p. 403 (1996).

The solid fat content of the composition-is-dependent on the wax content. For example, a blended composition containing about 1% of sunflower oil wax and vegetable oil has a SFC of about 0.3% at 10° C., whereas a composition containing 5% sunflower oil wax and vegetable oil has a SFC of about 4% to about 5.6% at 10° C.–37.8° C. A composition containing 10% sunflower oil wax and vegetable oil has a SFC of about 8.4% to about 10.5% at 10° C.–40° C. Interesterification of such a composition reduces the SFC to less than about 7.5% at temperatures of 21.1° C.–40° C. Similarly, a fat composition containing about 2% of rice bran wax has a SFC of about 1.7% to about 2.2% at 10° C.–37.8° C., whereas a fat composition containing about 7.5% of rice bran wax has a SFC of about 7% to about 8% at 10° C.–37.8° C.

Fat compositions of the invention can be formulated to be solid at room temperature. Hardness of a composition can be assessed according to AOCS Official Method Ce 16-60, using a cone penetrometer of a specified dimension and mass. In this method, a cone is dropped onto a prepared sample, and the relative hardness is determined by dividing the mass of the cone by the depth of the penetration. For example, a cone having a mass of 35 g is able to penetrate approximately 350 mm into a composition containing about 2% of sunflower oil wax and vegetable oil. In contrast, the penetration depth is about 20 mm for a composition containing about 7.5% of sunflower oil wax and vegetable oil. Thus, hardness increases with increasing amounts of wax.

Crystal structures of fat compositions containing canola oil and about 7.5% of sunflower oil wax, rice bran wax, or soybean stearin were examined microscopically. Compositions made with sunflower oil wax have a very long and fine needle shaped crystal, while compositions made with rice bran wax have a small, round shaped crystal. Fully hydrogenated soybean oil shows large, cluster shaped crystals, as the triglycerides in soy stearin tend to crystallize in the β-form. Without being bound by any particular theory, fine needle shaped crystals may have a stronger ability to build a network with liquid oil than other shaped crystals because they provide more surface area. Based on this theory, less sunflower oil wax is needed to hold liquid oil than either rice bran wax or fully hydrogenated soybean oil. In support of this theory, it was observed that 1% sunflower wax held canola oil without phase separation, while increased amounts of rice bran wax (4%) and soy stearin (10%) were needed to prevent separation.

Food Products

In applications such as plastic fat formulation, addition of a plant-derived wax component such as sunflower oil wax can reduce the amount of hardstock required, reducing the amount of total saturated fatty acids and total calories of the food products. In addition, compositions that contain a plant-derived wax component can be used to develop plastic fats having low or no trans fatty acids and low saturated fatty acids. Currently, trans fatty acids have to be replaced by saturated fatty acids to increase the solids in the fats. Replacing at least a portion of the saturated fats with a small amount of wax is an alternative way to increase the solid content of the fat, and can be used to produce margarine blends and shortenings. For example, a fat composition made from mid to high oleic canola oil (i.e., an oleic acid content of about 74% to about 90%) and sunflower oil wax can provide a solid product that is non-hydrogenated, and consequently low in trans fatty acids, e.g., less than 3%, as well as having a low saturated fatty acid content. Low saturated fatty acid content refers to less than 7% saturated fatty acids, e.g., 0–7%, 0.5–7.0%, 0.5–5.0%, 0.5–4%, or 0.5 –3% saturated fatty acids. As described herein, addition of sunflower oil wax to a vegetable oil provides a fat composition with a creamy appearance. In contrast, blends of soy stearin and oil produce a grainy appearance.

Although blended fat compositions are useful for certain applications, such as pie crusts and donuts, the compositions may have a waxy mouth feel and less than optimal spreadability due to the high melting point of the wax component. Interesterification of the composition can be used to rearrange the fatty acid distribution among TAGs and wax esters to further change the functional properties of the composition, including adjusting the melting point, leading to improved mouth feel, as well as improving the spreadability of the composition.

Plant-derived waxes are nonpolar and hydrophobic like TAGs. Unlike TAGs, however, waxes cannot be hydrolyzed by lipases or absorbed in the human digestive system. See, Seventh International Conference on Jojoba and Its Uses, 1988 Proceedings, Edited by A. R. Baldwin, AOCS, Champaign, Ill., pp. 354–363. Thus, compositions containing waxes can be used to formulate low calorie functional foods. Each gram of fat that is replaced with plant-derived waxes reduces the calorie content of the food product by nine calories.

For example, compositions of the invention can be used to prepare margarines or margarine blends. Margarines contain at least 80% fat, and typically are prepared from hydrogenated oil base stocks. Low trans margarines also are available, and typically contain oils such as hydrogenated palm and babassu oils (high in saturated fats) that have been interesterified. Other low trans margarines contain interesterified liquid oils. A fat composition containing about 0.1% to about 30% (e.g., 0.5% to 20%) of sunflower oil wax can be used as the basis for stick, tub, or soft margarines/spreads. A target SFI of a hard stick margarine is, for example, 28 at 10° C., 16 at 21.1° C., and 2% at 33.3° C. A target SFI for a soft spread is, for example, 11 at 10° C., 7 at 21.1° C., and 2 at 33.3° C. Margarines/spreads formulated with a fat composition of the invention also can include water, thickening agents such as gelatin, pectin, carrageenans, agar, or starch, milk products such as spray-dried whey, preservatives such as salt, sodium benzoate, potassium sorbate, and lactic acid, flavor agents, emulsifiers, vitamins, or coloring agents.

Shortenings also can be produced with fat compositions of the invention. For example, a fat composition containing about 0.1% to about 30% of a plant-derived wax component such as sunflower oil wax can be used to formulate a shortening. Emulsifiers, antifoam agents such as dimethylpolysiloxane, antioxidants such as tert-butylhydroquinone, butylated hydroxytoluene, and butylated hydroxyanisole, metal chelators such as citric acid, colorants such as carotenes, bixin, and apo-6-carotenal, and flavor agents such as diacetyl also can be added to shortening formulated with a fat composition of the invention.

Fat compositions of the invention also can be used to formulate, for example, spray oils, microwave popcorn products, which typically contain partially hydrogenated oils, or ice cream and ice cream coatings, which can be high in saturated fats or partially hydrogenated oils. Unpopped popcorn kernels can be coated with or suspended in a fat composition of the invention containing at least about 0.1% of a plant-derived wax component. In particular, a fat composition containing about 1% to about 2% of sunflower oil wax can be used to coat or suspend unpopped popcorn kernels. A popcorn product containing a fat composition of the invention also can include flavor and seasoning agents. Fat compositions of the invention can be used to replace a portion or all of the saturated fat or partially hydrogenated oils in an ice cream coating or a portion of the milk fat in ice cream. Ice cream or ice cream coating compositions also can include, for example, one or more of flavor agents, cocoa powder, sugar, lecithin, cream, and milk.

Non-food Uses of Fat Compositions

Fat compositions of the invention also can be used to formulate, for example, industrial greases, cosmetics such as lipsticks, chapsticks, and rouge, lotions, bulking agents, flavor carriers, paraffin substitutes, beverage clouding agents, pharmaceutical releasing agents, and encapsulating agents. Cosmetics and lotions formulated with a fat composition of the invention can contain, for example, one or more emulsifiers such as fatty alcohol ethoxylates, sorbitan fatty acid esters, or lanolin derivatives, thickeners such as carboxymethylcellulose or crosslinked polyacrylic acid, colorants, preservatives, and perfumes.

The invention will be further described in the following examples, which do not limit the scope of the invention described in the claims.

EXAMPLES

Example 1

Methods and Materials Oils and waxes: Pure sunflower oil wax and rice bran wax were obtained according to the method of U.S. Pat. No. 5,482,633. Soy stearin and high oleic canola oil (Clear Valley 75) were obtained from Cargill Oilseeds Division. Clear Valley 75 oil was obtained from IMC 130 seeds, which have an oleic acid content of about 75%, a linoleic acid content of about 12%, and an c-linolenic acid content of about 3.1%. See, U.S. Pat. No. 5,668,299. Sunflower oil sold under the name "NuSun™" and containing approximately 63% to 67% oleic acid, can be obtained from AgGrow Oils. Generic soybean oil and generic canola oil also were used. Oil-wax blends were prepared on a weight basis, and heated to 100° C. with stirring for about 5 min, such that the soy stearin and waxes were uniformly mixed with the canola or other vegetable oil.

Solid fat content (SFC): Solid fat contents were measured using a Bruker Minispec NMR (Milton, Ontario, Canada), according to AOCS Official Method Cd 16b-93.

Interesterification: Sodium methoxide was used as catalyst. One hundred grams of the oil-wax blend were dried at 105–110° C. under hose vacuum for one hour, cooled to about 100–105° C., and then about 0.5 grams of sodium methoxide were added to initiate interesterification. The appearance of a typical brownish red color in the oil was used as an indicator that interesterification had started. Interesterification was continued for 30 minutes to ensure completion. Reactions were stopped by addition of about 2 mL of a 10% citric acid solution, centrifuged at 5,000 rpm for 5 minutes, and the oil phase then was recovered and washed with about 8 ml of hot water. After removing the water phase by centrifugation, the oil phase was dried at 105–100° C. for 30 minutes.

Differential scanning calorimetry (DSC): Samples (approximately 10 mg) were loaded onto stainless steel pans and measured with a Perkin-Elmer DSC-7 calorimeter (Norwalk, Conn). The samples were melted by heating to 75° C. at a rate of 50° C./min, and held at 75° C. for 1 min. The temperature then was cooled to −40° C. at a rate of 20° C./min and held at −40° C. for 10 to 20 minutes. After this period of crystallization, the samples were heated to 75° C. or 80° C. at a rate of 10° C./min. Melting curves from −40° C. to 75° C. were reported and used to determine the progress of interesterification.

Penetration: The hardness of the oil wax blends was evaluated with a Precision (Bellwood, Ill.) penetrometer with a cone. Approximately 5 seconds after releasing the cone, penetration depths of the cone into the oil wax blend were recorded to the nearest 0.1 mm.

Crystal microscopic analysis: The oil-wax blends were melted at 80° C. A drop of each of the samples was placed on a slide and covered with a glass coverslip. Slides loaded with oil-wax mixtures were left overnight to crystallize. Microscopic pictures of the crystallized samples were taken with an Olympus BH-2 microscope.

Example 2

Characterization of wax oil blends Blends of canola oil, sunflower oil, and soybean oil and about 1% to about 10% of sunflower oil wax, rice bran wax, and soy stearin were prepared. After heating the wax (or stearin) to 100° C., vegetable oil was added and the mixture was stirred for about 5 minutes. Oil-wax or oil-stearin blends were left to cool to room temperature overnight to test the phase separation. It was observed that 1% sunflower wax held canola oil without phase separation, while increased amounts of rice bran wax (4%) and soy stearin (10%) were needed to prevent separation.

DSC melting curves of three blends made of about 7.5% wax or stearin and about 92.5% canola oil were obtained. The melting curves all had two peaks, one from canola oil at lower temperature and another from the waxes or stearin at higher temperature. The soy stearin blend had a valley area between the oil and fat peaks, which may be caused by interaction between the two components because of their structural similarity. The sunflower oil wax and rice bran wax blends did not have a valley between the oil and wax peaks, indicating that less interaction exists between triglycerides and linear long chain esters of waxes.

Table 1 shows the solid fat content (SFC) of these blends measured at selected temperatures by pulse-NMR. Although sunflower oil wax has more apparent liquid holding capacity, these "solids" do not correspond to NMR signals. At 10° C., soy stearin has the highest measurable solid content for all levels of blends, with rice bran wax giving a similar, but slightly lower solids content than soy stearin. Sunflower oil wax blends gave a lower solids content than both the soy stearin or rice bran wax blends. The NMR was calibrated for triglyceride fat analysis, which may account for some of the differences in molecular structure, molecular relaxation time, and proton amount between TAGs and wax esters. Nevertheless, the solids contents of all blends increased proportionally with an increased amount of soy stearin or waxes. When the temperature was increased to 26.6° C. and 37.8° C., the solids content in soy stearin blends decreased, most likely as a result of solubility of stearin in liquid oil with increasing temperature. No change in solid content was observed for the wax blends, possibly due to structural differences between the wax esters and liquid triglycerides.

TABLE 1

Solid fat content (SFC) of blends made of canola oil with soy stearin (SS), sunflower oil wax (SOW), and rice bran wax (RBW)

| % fat or wax in blend | SFC | | | | | | | | |
|---|---|---|---|---|---|---|---|---|---|
| | 10° C. | | | 26.7° C. | | | 37.8° C. | | |
| | SS | SOW | RBW | SS | SOW | RBW | SS | SOW | RBW |
| 1 | 1.3 | 0.3 | — | 1.3 | 0.3 | — | 0.6 | 0.3 | — |
| 2 | 2.9 | 1.6 | 2.2 | 1.7 | 1.6 | 2.0 | 0.9 | 1.7 | 2.3 |
| 3 | 4.2 | 2.5 | — | 3.2 | 2.4 | — | 2.2 | 2.3 | — |
| 4 | 4.9 | 3.4 | 4.4 | 3.6 | 4.0 | 4.0 | 3.6 | 3.4 | 4.1 |
| 5 | 6.9 | 5.6 | — | 5.6 | 5.1 | — | 4 | 5.1 | — |
| 7.5 | 8.8 | 6.2 | 8.2 | 7.7 | 6.2 | 8.1 | 5.2 | 6.8 | 7.4 |
| 10 | 11.8 | 9.2 | — | 9.8 | 9.6 | — | 7.8 | 10.3 | — |

These results indicate that waxes behave differently from solid TAGs physically in the oil bend, not only in the strength of network for holding liquid, but also in response to NMR solid detection signal. The solid contents of wax-oil blends increased proportionally with the increase of wax content.

The hardness of fats, which relates to solid fat content as well as crystal size and shape, was measured by the penetration of a cone. Since only sunflower oil wax formed a solid mixture with canola oil at room temperature and at low levels, these blends of sunflower oil wax and canola oil were tested with a cone penetrometer. FIG. 1 is a graph that indicates that the depth of penetration of the cone into these blends decreases with an increase of wax content. This indicates that the hardness of oil-wax blends increases with an increased amount of wax.

A blend of 10% sunflower oil wax and canola oil was interesterified with 0.5% sodium methoxide at 100° C. With addition of sodium methoxide, the oil-wax blend showed a typical brown reddish color that is used as the indicator for a successful initiation of interesterification of oils and fats. Without being limited by theory, after interesterification, the solid content decreased dramatically, indicating that the unsaturated fatty acids of the liquid oil esterified with the fatty alcohols and that long chain saturated acyl groups from the wax were incorporated into the liquid oils (TAGS) (Table 2). DSC melting curves were obtained for the interesterified compositions. The typical peak disappeared and several new peaks appeared on the DSC melting curve after interesterification. This interesterified wax-oil blend has an improved spreadability and plasticity with similar creamy appearance to the original blend.

TABLE 2

SFC of sunflower oil wax-canola oil blends (10:90) before and after interesterification.

| Sample | SFC | | | |
|---|---|---|---|---|
| | 21.1° C. | 26.7° C. | 33.3° C. | 40° C. |
| Before | 10 | 9.6 | 9.7 | 10.6 |
| After | 5.7 | 3.8 | 1.6 | 1.1 |

The solid fat content of compositions made with generic canola oil, NuSun™ sunflower oil, or generic soybean oil, and 5% or 10% sunflower oil wax was assessed by NMR, as described above. As shown in Table 3, vegetable oils containing 10% sunflower oil wax had a SFC that ranged from about 8.47 to 9.03% at 10° C., about 8.57 to 9.42% at 21.1° C., 8.98 to 9.61 at 26.7° C., 9.51 to 10.25% at 33.3° C., 9.77 to 10.4% at 37.8° C., and 9.81 to 10.32% at 40° C. In general, interesterification decreased the SFC. For example, an interesterified (INES) composition of NuSun™ and 10% sunflower oil wax had a SFC profile of 9.27, 6.04, 4.61, 3.47, 2.73, and 2.95% at 10° C., 21.1° C., 26.7° C., 33.3° C, 37.8° C., and 40° C., respectively. In comparison, the non-esterified composition had a SFC of 8.47, 8.57, 9.13, 9.51, 9.77, and 9.81% at 10° C., 21.1° C., 26.7° C., 33.3° C., 37.8° C., and 40° C., respectively. Interesterification of the canola oil composition shown in Table 3 did not appear to be complete.

TABLE 3

SFC of sunflower oil wax and vegetable oil blends and interesterified compositions

| SAMPLE | SFC | | | | | |
|---|---|---|---|---|---|---|
| | 10° C. | 21.1° C. | 26.7° C. | 33.3° C. | 37.8° C. | 40° C. |
| Canola 5%* | 4.05 | 4.18 | 4.12 | 4.74 | 4.67 | 4.72 |
| NuSun ™ 5% | 4.15 | 4.49 | 3.96 | 4.48 | 4.77 | 4.62 |
| Soy 5% | 4.10 | 4.22 | 4.18 | 4.77 | 4.61 | 4.63 |
| Canola 10% | 9.03 | 9.42 | 9.61 | 10.25 | 10.40 | 10.32 |
| NuSun ™ 10% | 8.47 | 8.57 | 9.13 | 9.51 | 9.77 | 9.81 |
| Soy 10% | 8.67 | 8.91 | 8.98 | 9.73 | 9.89 | 10.14 |
| INES Canola 10% | 9.58 | 8.49 | 8.25 | 8.28 | 8.39 | 8.4 |
| INES NuSun ™ 10% | 9.27 | 6.04 | 4.61 | 3.47 | 2.73 | 2.95 |
| INES Soy 10% | 10.12 | 7.62 | 6.07 | 5.59 | 5.35 | 5.5 |

*Percentages indicate the amount by weight of sunflower oil wax.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition, said composition comprising a non-hydrogenated vegetable oil and a plant-derived wax component selected from the group consisting of sunflower oil wax, rice bran wax, and corn oil wax, wherein said plant-derived wax component comprises about 0.5% to about 15%, by weight, of said composition, and wherein said composition has a melting point of at least about 46° C.

2. The composition of claim 1, wherein said plant-derived wax is sunflower oil wax.

3. The composition of claim 1, wherein said non-hydrogenated vegetable oil is selected from the group consisting of rapeseed oil, soybean oil, sunflower oil, palm oil, safflower oil, coconut oil, palm kernel oil, sesame oil, peanut oil, cottonseed oil, and corn oil.

4. The composition of claim 3, wherein said vegetable oil is rapeseed oil.

5. The composition of claim 4, wherein said rapeseed oil is canola oil.

6. The composition of claim 1, wherein said composition comprises a trans fatty acids content of about 0%.

7. The composition of claim 1, wherein said composition comprises a trans fatty acids content of less than about 3%.

8. The composition of claim 1, wherein said composition comprises a saturated fatty acid content of less than 7%.

9. The composition of claim 1, wherein said plant-derived wax component comprises about 0.5% to about 30%, by weight, of said composition.

10. The composition of claim 1, wherein said plant-derived wax component comprises about 0.5% to about 7.5%, by weight, of said composition.

11. The composition of claim 1, wherein said plant-derived wax component comprises about 1% to about 5%, by weight, of said composition.

12. The composition of claim 1, wherein said plant-derived wax component comprises about 2% to about 4%, by weight, of said composition.

13. The composition of claim 1, wherein said composition has a melting point of at least about 52° C.

14. The composition of claim 1, wherein said composition has a melting point of at least about 60° C.

15. The composition of claim 1, wherein said composition has a melting point of about 46° C. to about 75° C.

16. A composition comprising a non-hydrogenated vegetable oil and a plant-derived wax component selected from the group consisting of sunflower oil wax, rice bran wax, and corn oil wax, wherein said plant-derived wax component comprises about 0.5% to about 15%, by weight, of said composition, and wherein said composition has a melting point of about 5° C. to about 50° C.

17. A margarine or spread comprising the composition of claim 16.

18. A shortening comprising the composition of claim 16.

19. A The composition of claim 16, wherein said plant-derived wax component is selected from the group consisting of sunflower oil wax, rice bran wax, hydrogenated jojoba oil, and corn oil wax.

20. The composition of claim 16, wherein said plant-derived wax is sunflower oil wax.

21. The composition of claim 16, wherein said vegetable oil is selected from the group consisting of rapeseed oil, soybean oil, sunflower oil, palm oil, safflower oil, coconut oil, palm kernel oil, sesame oil, peanut oil, cottonseed oil, and corn oil.

22. The composition of claim 21, wherein said vegetable oil is rapeseed oil.

23. The composition of claim 20, wherein said rapeseed oil is canola oil.

24. The composition of claim 16, wherein said plant-derived wax component comprises about 0.1% to about 30%, by weight, of said composition.

25. A composition comprising a non-hydrogenated vegetable oil from a first plant species and a plant-derived wax component from a second plant species, wherein said plant-derived wax component is a sunflower oil wax and comprises about 0.5% to about 15%, by weight, of said composition.

26. A food product comprising a fat composition, said fat composition comprising a non-hydrogenated vegetable oil and a plant-derived wax component selected from the group consisting of sunflower oil wax, rice bran wax, and corn oil wax, said plant-derived wax component comprising at least about 0.1%, by weight, of said fat composition.

27. The food product of claim 26, wherein said vegetable oil and said plant-derived wax component in said fat composition are interesterified.

* * * * *

UNITED STATES PATENT AND TRADEMARK OFFICE
CERTIFICATE OF CORRECTION

PATENT NO. : 6,582,748 B1
DATED : June 24, 2003
INVENTOR(S) : Willie H-T Loh, Linsen Liu and Daniel S. Lampert It is certified that error appears in the above-identified patent and that said Letters Patent is hereby corrected as shown below:

<u>Column 13,</u>
Line 6, please delete "claim 20" and insert -- claim 22 -- therefor.

Signed and Sealed this

Sixteenth Day of December, 2003

JAMES E. ROGAN
*Director of the United States Patent and Trademark Office*